United States Patent [19]

Fryberger et al.

[11] 4,199,974
[45] Apr. 29, 1980

[54] EOLIAN SAND TRAP

[75] Inventors: Steven G. Fryberger, Golden; Thomas S. Ahlbrandt, Lakewood, both of Colo.

[73] Assignee: The United States of America as represented by the Secretary of the Interior, Washington, D.C.

[21] Appl. No.: 942,847

[22] Filed: Sep. 15, 1978

[51] Int. Cl.² .......................... G01N 1/04; G01N 1/22
[52] U.S. Cl. ..................................... 73/28; 73/421.5 R
[58] Field of Search ............... 73/28, 170 R, 421.5 R, 73/421 A; 55/270, 456, 442, 443

[56] References Cited

U.S. PATENT DOCUMENTS

| | | | |
|---|---|---|---|
| 1,855,381 | 4/1932 | Bobar | 55/443 |
| 2,353,828 | 7/1944 | Hyde | 55/315 |
| 2,973,642 | 3/1961 | Grinnel | 73/28 |
| 3,587,323 | 6/1971 | Bejaminson | 73/421.5 R |
| 3,715,911 | 2/1973 | Chuan | 73/28 |

*Primary Examiner*—S. Clement Swisher
*Assistant Examiner*—Denis E. Corr
*Attorney, Agent, or Firm*—Thomas Zack; Donald A. Gardiner

[57] ABSTRACT

A trapping and measuring device is provided for collecting and weighing wind borne particles of sand in the desert or the like. The device includes a rotatable trapping housing which is constructed to permit the wind to pass therethrough while trapping the sand carried by the wind. The column-like housing is mounted on a fixed base which contains a funnel and collector cup assembly together with a transducer for weighing the sand collected in the cup. A wind-catching plate attached to the rotatable housing provides orientation of the housing entrance openings so as to face the wind. A tortuous path provided within the trapping housing promotes release of the sand from the wind passing through the housing and screens at the exits block egress of the sand.

7 Claims, 6 Drawing Figures

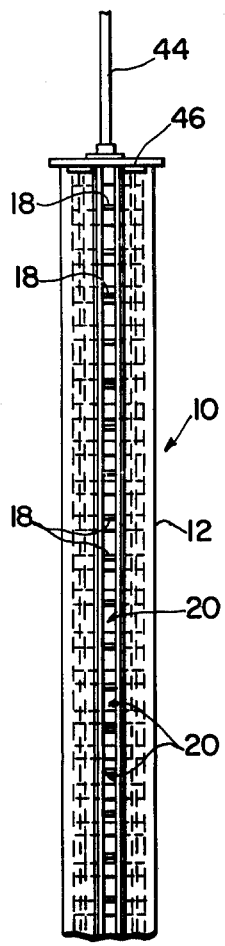
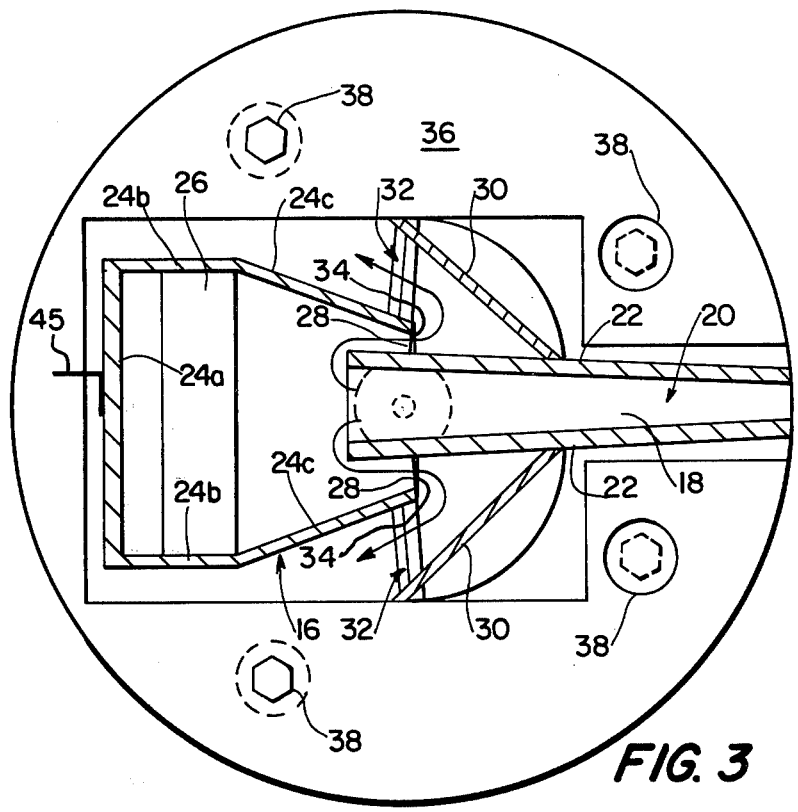
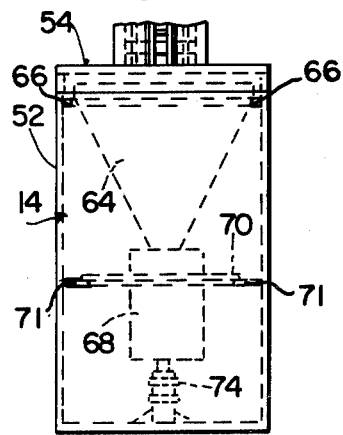
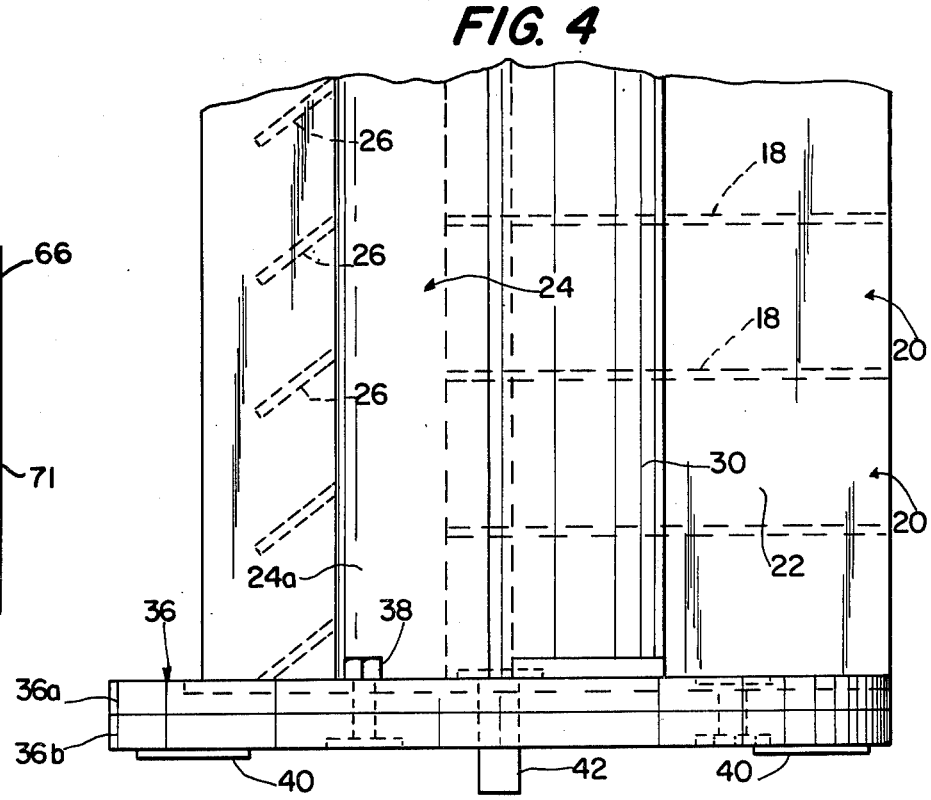

EOLIAN SAND TRAP

FIELD OF THE INVENTION

The invention relates to a device for trapping and automatically weighing sand borne by the wind.

BACKGROUND OF THE INVENTION

Information with regard to the rate of sand migration in deserts, beaches and the like is of interest to many geologists as well as other persons in the scientific community. Some devices have been developed for trapping and collecting wind driven sand. These devices take a variety of forms and, in general, provide some form of entrance opening or openings through which the sand enters the trap and a collection chamber to which the sand falls by gravity. The sand collected in the collection chamber is removed therefrom for weighing to thereby enable one to determine the amount of sand which has moved through an area during a given period. A number of sand traps were evaluated in Horikawa, K. and Shen, H. W., "Sand Movement by Wind Action", Beach Erosion Board, Office of the Chief of Engineers, Technical Memorandum No. 119, Dept. of the Army, Corps. of Engineers, (U.S.A.), 51 pp. and appendices (1960). A further background reference of interest is Bagnold, R. A., "Physics of Blown Sand and Desert Dunes", Meuthen, London, 265 pp. (1954). Other work in this area, including the design of a sand and soil aggregate catching device, has been done by U.S. Department of Agriculture, Wind Erosion Laboratory, Manhattan, Kansas. A distinction should be made between particles in suspension and sand drift migration by wind action. The latter is generally thought to be comprised of three distinct sub-processes, viz., (i) saltation, (ii) suspension and (iii) surface creep. As defined in the A.G.I. Glossary published by the American Geological Institute, Washington, D.C. (1973), saltation is a mode of sediment transport in which the particles are moved progressively forward in a series of short intermittent leaps, jumps, hops or bounces from a bottom surface. Examples are sand particles which "skip" downwind by impact and rebound along a desert surface, or "bounce" downstream under the influence of eddy currents that are not turbulent enough to retain the particles in suspension and thereby return the particles to the stream bed at some distance downstream. Suspension is defined as a mode of sediment transport in which upward currents in eddies of turbulent flow are capable of supporting the weight of undissolved sediment particles and indefinitely holding and maintaining the particles in the surrounding fluid. Examples are silt in water and dust in air. Surface creep is the slow downwind advance of large sand grains along a surface by impact of smaller grains in saltation.

There are, of course, many examples of devices used in trapping and/or collecting particles in suspension, e.g., dust collectors, and the like. Examples of such devices are disclosed in U.S. Pat. Nos. 1,437,866 (Shurtleff); 2,353,828 (Hyde); 2,962,122 (Linderoth); 3,296,858 (Doury et al); 3,787,123 (Sigrist); 3,914,979 (Shofner).

SUMMARY OF THE INVENTION

According to the present invention, a sand trapping device is provided which possesses a number of important advantages over sand traps of the prior art. For example, the sand trapping device of the invention provides instantaneous, on site measurement of the weight of sand collected by the trap which, with the addition of a telemetry capability and other devices, mainly to empty the trap of sand periodically, would make possible instantaneous, remote (unattended) observation. The trapping and measuring device of the invention is a variable direction (Eolian) trap and is constructed as to swing with changes in the wind direction so as to face the wind. In addition, the trapping device of invention is able to catch more sand than prior art sand traps (trapping nearly all of the sand) and, moreover, to retain more of the sand trapped (e.g., by preventing sand loss through the side ports). Because of these features, and the low aerodynamic resistance to flow and minimal back pressure resulting in minimal sand particle deflection, the device of the invention provides more accurate measurements than devices of the prior art.

In accordance with the invention, a trapping and measuring device for wind borne particles of sand is provided which comprises a housing including trapping means for permitting wind to pass therethrough while trapping sand borne by the wind, the trapping means including an entrance opening through which the sand bearing wind enters the housing, an exit through which the wind can pass from the housing and a baffle arrangement positioned between the opening and exit for intercepting the wind during the travel thereof between the opening and exit to thereby promote release of the sand particles from the wind; collecting means for collecting sand trapped by the trapping means; and weighing means for weighing the sand collected by said collecting means and providing an output in accordance therewith.

The sand trapping housing is rotatably mounted so that the opening in the housing faces in the direction in which the wind is blowing. A wind-catching plate or sheet is secured to the rotatable housing provides the appropriate orientation. In addition, a further, fixed housing is provided in which said collecting means and said weighing means are located, this fixed housing preferably including a hinged cover for permitting access to the collecting means and the weighing means. The collecting means advantageously comprises a collector cup and the hinged cover permits the cup to be readily removed for field changes. The weighing means preferably compries an electromechanical transducer which produces an electrical output signal in accordance with the weight of the sand collected by the collecting means. Further, the baffle arrangement includes a pair of straight, slanted baffle plates located rearwardly of said entrance opening on opposite sides of the means defining said entrance opening. This feature, while not novel per se, serves in combination with the other features discussed above (as well as hereinafter) to provide the increased accuracy referred to previously. A further feature which enhances accuracy is the provision of screening (#200 mesh) at the exits so as to prevent loss of sand sized particles through these exits.

The rotatable housing includes a central support located on the top thereof, and the device further comprises a plurality of guy wires attached to the support port for supporting said housing in an upright position. This simple arrangement enables a relatively tall housing to be easily supported for rotation.

The device of the present invention, when used in conjunction with wind speed measuring equipment, can be employed to determine the rate of sand drift (migration) as a function of wind speed for scientific purposes. More generally, the device of the invention can be used for site evaluation possible sand drift across roads and the like as well as in scientific research of eolian processes. The invention also has military applications in the siting of airfields, installations and the like with respect to sand storms.

Other features and advantages of the invention will be set forth in, or apparent from, the detailed description of a preferred embodiment found hereinbelow.

BRIEF DESCRIPTION OF THE DRAWINGS

FIG. 2 is a front elevational view of the device of FIG. 1;

FIG. 3 is a transverse cross-sectional view, drawn to an enlarged scale, of the trapping portion of the device of FIG. 1;

FIG. 4 is a detail of the lower end of the trapping portion of the device of FIG. 1, drawn to the same scale as FIG. 3;

DESCRIPTION OF THE PREFERRED EMBODIMENT

Figure 1:
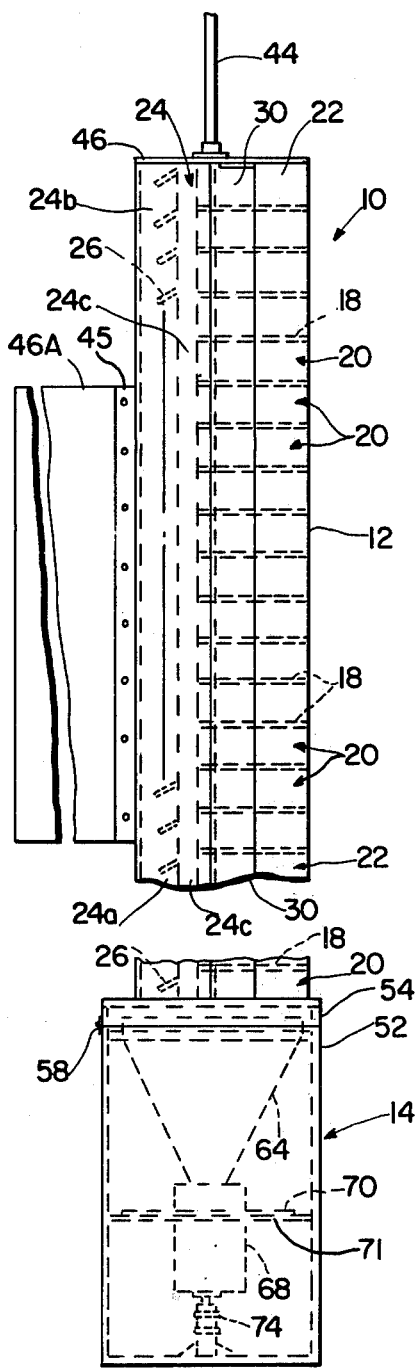
FIG. 1 is a side elevational view, with parts broken away, of a preferred embodiment of the sand trapping and measuring device of the invention.

Referring to the drawings and particularly to FIGS. 1 and 2, there is illustrated a preferred embodiment of the Eolian sand trap of the invention. The sand trap, which is generally denoted 10, includes an upper housing or trapping portion 12 which serves to trap the sand and which is rotatably mounted on a fixed base or collector portion 14 which serves to collect and weigh the sand trapped by the upper trapping portion 12. The basic components of both the rotary trap housing 12 and stationary collector 14 are preferably fabricated of a suitable plastic.

As illustrated in FIGS. 1 to 4, trapping portion 12 comprises an elongate, vertically extending chamber 16 (seen in cross section in FIG. 3) the front part of which is divided vertically by a series of horizontal partitions 18 which define the top and bottom walls of a series of vertically spaced entrance openings 20. As illustrated in FIG. 3, each entrance opening 20 is also defined by side walls 22 which are inclined toward the front of the chamber 16 so as to provide that the width of inlet opening increases along the length thereof proceeding rearwardly.

Entrance openings 20 terminates in a mixing chamber 24 which extends from the top to the bottom of trapping housing 12 and which includes a series of vertically spaced, inclined deflector plates or deflectors 26 which deflect the sand exiting from the entrance openings 20 downwardly toward the bottom of housing 12.

Mixing chamber 24 includes a rear wall 24a and a pair of straight side walls 24b in addition to a pair of slanted side walls 24c at the forward end thereof. The latter are laterally spaced from the side walls 22 of entrance openings 20 to form a pair of chamber exit gaps or openings 28 on opposite sides of the side walls 22 of entrance openings 20. A pair of inclined outer walls 30 extend outwardly at an angle from the side walls 22 of entrance openings 20 at a point roughly midway along the length of the latter so as to be positioned generally opposite gaps 28 is forced rearwardly as indicated by the arrows and any sand suspended therein will have a tendency continue in flight, striking deflectors 26 and falling down inside of mixing chamber 24.

A further pair of outlet gaps or openings 32 are defined between the forward edges of side walls 24c of chamber 24 and the rearward edges of the inclined outer walls 30. A pair of strips of a mesh or screen material, individually denoted 34, are disposed in respective ones of the exit openings 28 so as to prevent any sand suspended in the air passing through openings 28 from exiting along with the air. Thus, the sand-bearing air enters chamber 16 through a relatively narrow entrance opening 20 from whence it follows the sinuous or S-shaped path illustrated in FIG. 3 through the chamber exit gaps 28 and out through the exit openings 32.

Chamber 16 is supported on a circular mounting plate or base plate 36 best seen in FIGS. 3 and 4 and formed by a pair of plates 36a, 36b joined together by four cap nut and flat head bolt assemblies 38, as illustrated. Felt seals, indicated schematically at 40, are located around the circular opening is the housing cover so as to engage the outer surface of the base plate 36 and prevent direct entrance of sand into the trap. A centrally located lower bearing shaft or stub shaft 42, preferably fabricated of metal, extends below the lower surface of base plate 36 and provides a pivot axis about which trap housing 12 rotates. A support shaft 44 (see FIGS. 1 and 2) is mounted on a top plate 46 located at the upper end of housing 12.

Figure 6:
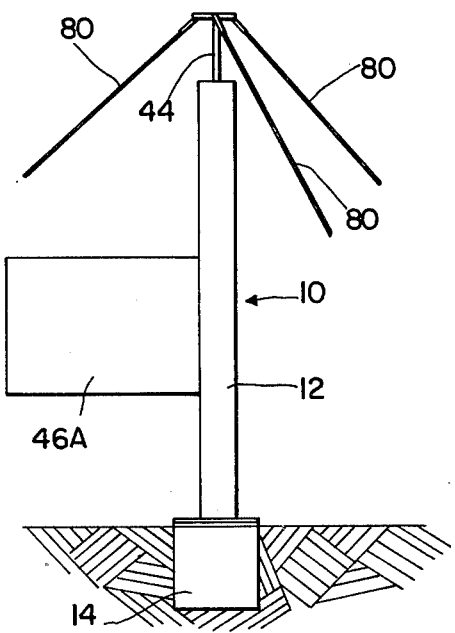
FIG. 6 is a schematic representation of the device of FIG. 1, in use.

Referring again to FIG. 1, an angle mount member 45, which is fabricated of aluminum and one leg of which is secured to the rear wall 24a of trap housing 12, serves to mount a wind-catching sheet or plate 46A fabricated of aluminum, Plexiglass or the like (see also FIG. 6). Sheet 46A provides a broad surface area for catching the wind, and the force of the wind thereon will cause housing 12 to pivot or swing in a direction such that the wind forces are on sheet 46A are at minimum, i.e., so that the sheet 46A extends parallel to the wind, and hence that the entrance openings 20 face into the wind.

Figure 5:
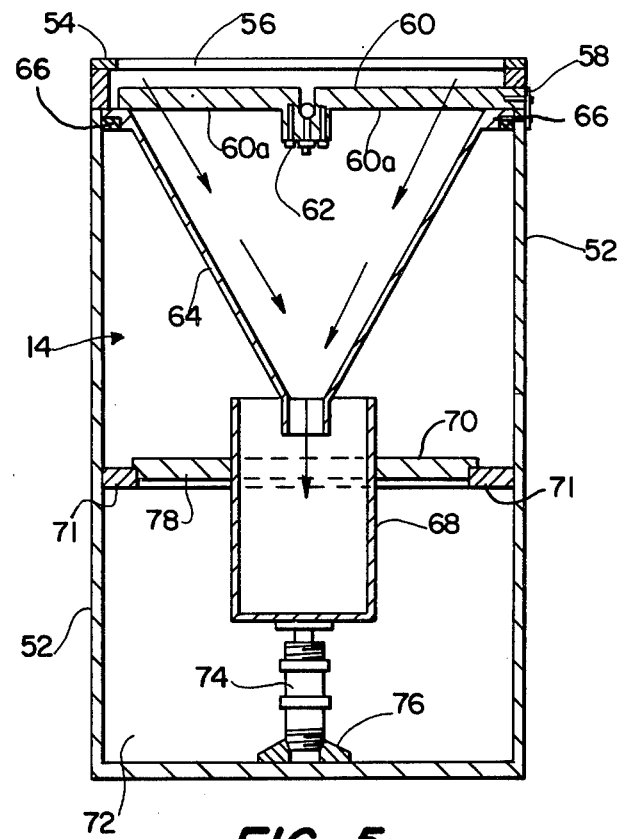
FIG. 5 is a cross-sectional view, drawn to an enlarged scale, of the collecting and measuring portion of the device of FIG. 1.

Referring to FIGS. 1, 2 and 5, and particularly the latter, collector 14 comprises a generally box like housing 52 including a housing cover 54. Cover 54 includes a central cylindrical aperture 56 therein and is movably connected to the upper edge of housing 52 by a hinge 58. Fall-away latches (not shown) provide quick opening of cover 54. These features permit ready removal of the contents of housing 52 and enable changing of the same under field conditions, e.g., during sandstorms.

The contents of housing 52 include a bearing support member 60 which, in a preferred embodiment, comprises four equally spaced radial aluminum support arms 60a (two of which are shown in FIG. 5) which define sector shaped openings therebetween through which the sand falls. The support arms 60a mount a main bearing 62 in which the lower bearing shaft 42 (see FIG. 4) is received. A funnel 64 is supported by a support rim 66 located at the upper end of housing 52. A collector cup 68 is disposed beneath the lower end of funnel 64 and extends through an annular shield 70 which prevents sand from reaching a lower compartment 72. Shield 70 is mounted on a further support rim 71 which extends from the wall of housing 52.

Cup 68 is supported on a transducer 74 which is located within lower compartment 72 and which itself is supported by a transducer base member 76. (See FIG. 5) Transducer 74 preferably comprises a conventional Schaevitz Inc. load cell which provides, when used with an appropriate display panel a digital readout of the weight of the sand collected in cup 68. Transducer 74 can be utilized in combination with suitable telemetry (not shown) including a transmitter and a remote readout or display unit to enable remote monitoring of the amount of sand collected.

Referring to FIG. 6, a schematic representation is provided of the sand trap of the invention in use. The trap is supported in a vertical orientation by a series of three cables 80 which are connected between the top of upper support shaft 44 and the ground. The collector portion 14 is mounted in the ground as indicated. As noted above, wind-catching sheet 46A provides appropriate orientation of rotatable, trap housing 12 by intercepting the wind and providing rotation of trap housing 12 responsive thereto so as to orient housing 12 with entrance openings 20 facing the wind.

Briefly considering the operation of the sand trap of the invention as described above, the sand bearing wind enters entrance openings 20 and eventually passes out from trapping portion 12 through gaps or passages 28 and 32. The bulk of the sand carried by the wind falls by its own weight or is deflected downwardly by deflectors 26 and the tortuous path provided, in cooperation with screens 34, ensures that virtually all of the sand entering trap 10 is retained therein. The sand trapped by trapping housing 12 will fall downwardly through funnel 64 to cup 68 wherein it is collected. The weight of the sand in collector cup 68 is measured by transducer 74 which produces an electrical output signal in accordance therewith. As described, this output signal can be relayed to a remote monitoring site using a cable, and the weight read on the digital readout (not shown). In contrast to prior art sand traps, the trapping housing 12 is at least four or five feet in height so as to ensure that virtually all of the sand carried by the wind along the ground will be captured by the trap 10.

Although the invention has been described relative to an exemplary embodiment thereof, it will be understood that other variations and modifications can be effected in this embodiment without departing from the scope and spirit of the invention.

We claim:

1. A trapping and measuring device for wind borne particles of sand, said device comprising:
   a housing including trapping means for permitting wind to pass therethrough while trapping sand borne by the wind, said trapping means including means defining an entrance opening through which the sand-bearing wind enters said housing, exit means for providing an exit through which the wind can pass from said housing and baffle means positioned between said opening and said exit means for intercepting the wind during the travel thereof between said opening and said exit means to thereby promote release of the sand particles from the wind, said baffle means including a pair of straight, slanted baffle plates located rearwardly of said entrance opening on opposite sides of the means defining said entrance opening so as to define a pair of said exits;
   collecting means for collecting sand trapped by said trapping means; and
   weighing means for weighing the sand collected by said collecting means and providing an output in accordance therewith.

2. A trapping and measuring device for wind borne particles of sand, said device comprising:
   a housing including trapping means for permitting wind to pass therethrough while trapping sand borne by the wind, said trapping means including means defining an entrance opening through which the sand-bearing wind enters said housing, exit means for providing an exit through which the wind can pass from said housing and baffle means positioned between said opening and said exit means for intercepting the wind during the travel thereof between said opening and said exit means to thereby promote release of the sand particles from the wind;
   collecting means for collecting sand trapped by said trapping means;
   weighing means for weighing the sand collected by said collecting means and providing an output in accordance therewith; and
   further comprising screen means for preventing sand from passing out of said exit.

3. A trapping and measuring device for wind borne particles of sand, said device comprising:
   a housing including trapping means for permitting wind to pass therethrough while trapping sand borne by the wind, said trapping means including means defining an entrance opening through which the sand-bearing wind enters said housing, exit means for providing an exit through which the wind can pass from said housing and baffle means positioned between said opening and said exit means for intercepting the wind during the travel thereof between said opening and exit means to thereby promote release of the sand particles from the wind;
   collecting means for collecting sand trapped by said trapping means;
   weighing means for weighing the sand collected by said collecting means and providing an output in accordance therewith;
   means for rotatably mounting said housing so that the opening in said housing faces in the direction in which the wind is blowing;
   a fixed housing in which said collecting means and said weighing means are located, said fixed housing including a hinged cover for permitting access to said collecting means and said weighing means; and
   felt seal located between the rotary housing and said fixed housing.

4. A trapping and measuring device for wind borne particles of sand, said device comprising:
   a housing including trapping means for permitting wind to pass therethrough while trapping sand borne by the wind, said trapping means including means defining at least two entrance openings through which the sand-bearing wind enters said housing, exit means for providing an exit through which the wind can pass from said housing and baffle means positioned between said openings and said exit means for intercepting the wind during the travel thereof between said opening and said exit means to thereby promote release of the sand particles from the wind, said baffle means including a pair of straight, slanted baffle plates located rearwardly of its entrance opening on opposite sides of the means defining the entrance opening so as to define a pair of said exits;

means for preventing sand from escaping from said exit;

collecting means for collecting sand trapped by said trapping means; and weighing means for weighing the sand collected by said collecting means and providing an output in accordance therewith.

5. A trapping and weighing device as claimed in claim 4 said means for preventing being screen means located upstream of said exits for preventing sand from passing out of said exits.

6. A trapping and measuring device for wind borne particles of sand, said device comprising:

a housing including trapping means for permitting wind to pass therethrough while trapping sand borne by the wind, said trapping means including means defining at least two entrance openings through which the sand-bearing wind enters said housing, exit means for providing an exit through which the wind can pass from said housing and baffle means positioned between said opening and said exit means for intercepting the wind during the travel thereof between said opening and said exit means to thereby promote release of the sand particles from the wind;

screen means for preventing sand from escaping from said exit;

collecting means for collecting sand trapped by said trapping means; and weighing means for weighing the sand collected by said collecting means and providing an output in accordance therewith.

7. A trapping and measuring device for wind borne particles of sand, said device comprising:

a housing including trapping means for permitting wind to pass therethrough while trapping and borne by the wind, said trapping means including means defining at least two entrance openings through which the sand-bearing wind enters said housing, exit means for providing an exit through which the wind can pass from said housing and baffle means positioned between said opening and said exit means for intercepting the wind during the travel thereof between said opening and exit means to thereby promote release of the sand particles from the wind;

means for preventing sand from escaping from said exit;

collecting means for collecting sand trapped by said trapping means;

weighing means for weighing the sand collected by said collecting means and providing an output in accordance therewith;

means for rotatably mounting said housing so that the openings in said housing face in the direction in which the wind is blowing;

a fixed housing in which said collecting means and said weighing means are located, said fixed housing including a hinged cover for permitting access to said collecting means and said weighing means; and felt seals located between the rotary housing and said fixed housing.

* * * * *